(12) United States Patent
Middlesworth et al.

(10) Patent No.: US 6,472,084 B1
(45) Date of Patent: Oct. 29, 2002

(54) TEAR-RESISTANT LOW SET ELASTIC FILM AND METHOD OF MAKING

(75) Inventors: Jeffrey A. Middlesworth, Wauconda; James W. Cree, Mundeelein; Steve D. Bruce, Crystal Lake, all of IL (US)

(73) Assignee: Tredegar Film Products Corporation, Richmond, VA (US)

( * ) Notice: Subject to any disclaimer, the term of this patent is extended or adjusted under 35 U.S.C. 154(b) by 0 days.

(21) Appl. No.: 09/504,246

(22) Filed: Feb. 15, 2000

(51) Int. Cl.$^7$ .............................................. B32B 27/08
(52) U.S. Cl. ....................... 428/517; 428/156; 428/332; 428/523
(58) Field of Search ................................ 428/156, 500, 428/515, 516, 517, 523, 332

(56) References Cited

U.S. PATENT DOCUMENTS

| | | | |
|---|---|---|---|
| 4,300,967 A | 11/1981 | Sigl | 156/164 |
| 4,350,655 A | 9/1982 | Hoge | 264/145 |
| 4,368,565 A | 1/1983 | Schwartz | 26/99 |
| 4,476,180 A | 10/1984 | Wnuk | 428/220 |
| 4,777,073 A | 10/1988 | Sheth | 428/155 |
| 4,880,682 A | 11/1989 | Hazelton et al. | 428/152 |
| 4,892,903 A | 1/1990 | Himes | 524/488 |
| 5,167,897 A | 12/1992 | Weber et al. | 264/288.8 |
| 5,344,691 A | 9/1994 | Hanschen et al. | 428/152 |
| 5,354,597 A | 10/1994 | Capik et al. | 428/152 |
| 5,395,471 A | 3/1995 | Obijeski et al. | 156/244.11 |
| 5,429,856 A | 7/1995 | Krueger et al. | 604/370 |
| 5,501,679 A | 3/1996 | Krueger et al. | 604/393 |
| 5,691,034 A | 11/1997 | Krueger et al. | 428/152 |
| 5,733,628 A | 3/1998 | Pelkie | 428/138 |
| 5,840,412 A | 11/1998 | Wood et al. | 428/284 |
| 5,993,432 A | 11/1999 | Lodge et al. | 604/385.2 |

FOREIGN PATENT DOCUMENTS

| | | |
|---|---|---|
| EP | 0 703 068 A2 | 6/1993 |
| EP | 0521 883 B1 | 8/1996 |

OTHER PUBLICATIONS

"SEF: A New Elastic Film for the Hygiene Industry", Nordenia Technologies, pp. 1–4, date of first publication unknown, but published at least as early as Apr. 1999.

Baldaug, Georg, "Zero Stain Film for Elastic Diaper Components", Nordenia Technologies GbmH, pp. 1–6, date of first publication unknown, but published at least as early as Mar. 1999.

Primary Examiner—Blaine Copenheaver
Assistant Examiner—Christopher Paulraj
(74) Attorney, Agent, or Firm—Jenkens & Gilchrists, P.C.

(57) ABSTRACT

A tough low set elastic film exhibiting surprisingly high tear resistance and method of making the same. The film of the invention is especially beneficial when holes form on the films during manufacturing or normal wear and method of making. The film has activated and non-activated zones formed during an activation process. The activated zones allow the film to expand without generating excessive tensional forces. The film has M-polypropylene or M-polyethylene skin layers and a core layer having an elastomeric polyurethane, ethylene copolymer such as ethylene vinyl acetate styrenic elastomer, an ethylene/propylene copolymer elastomer or ethylene/propylene/diene terpolymer elastomer. The activation process allows the skin layers to behave more like the core layer.

21 Claims, 3 Drawing Sheets

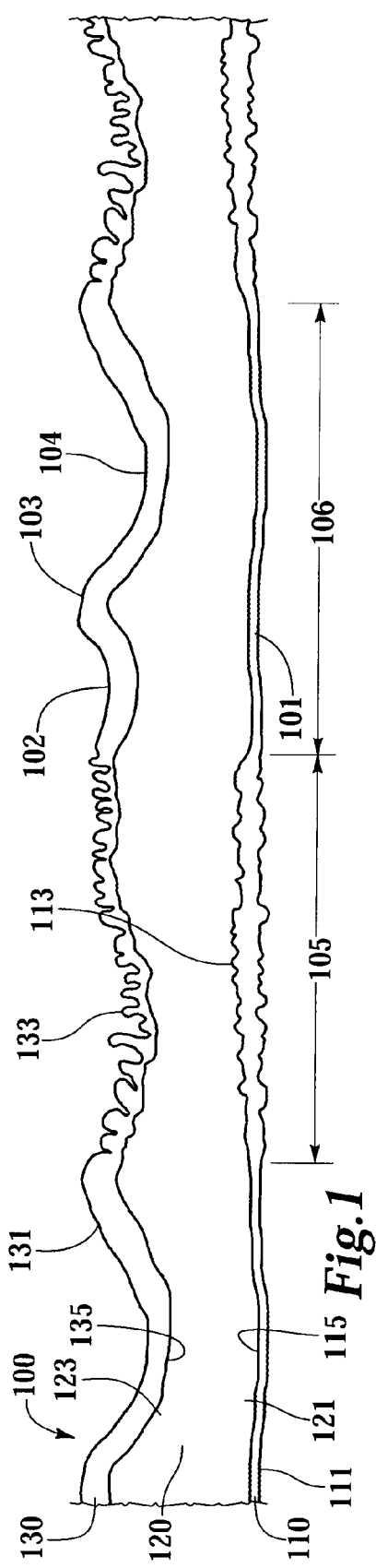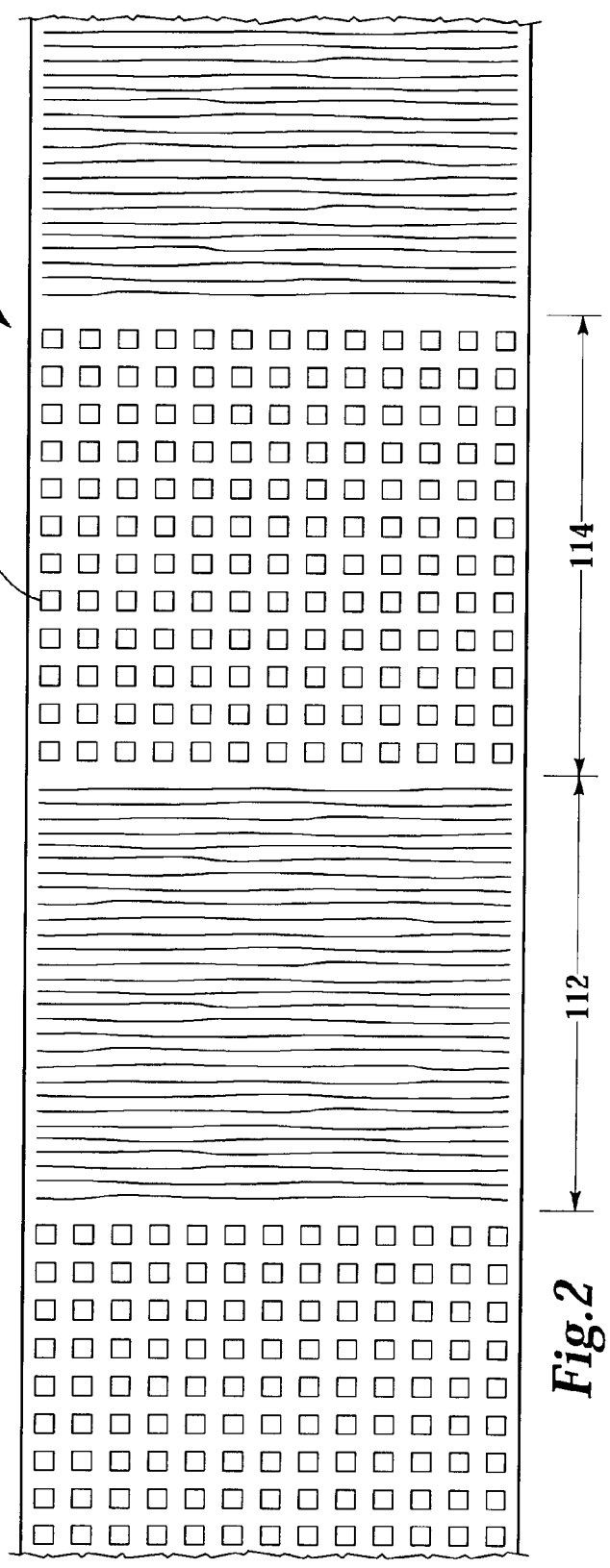

TEAR-RESISTANT LOW SET ELASTIC FILM AND METHOD OF MAKING

BACKGROUND

The present invention relates to elastic films, and more particularly, to elastic films having high tear-strength and low set. Elastic films of the present invention having high tear-strength and low set exhibit surprisingly high tear resistance, especially when holes form on the films.

Elastic films of the present invention have a wide range of potential uses in both durable and disposable articles, but are particularly well suited for use in elastic waistbands and in products including absorbent products and the like.

SUMMARY OF THE INVENTION

The present invention relates to the coextrusion of a thin multi-layer elastic film that stretches in the transverse direction. The elastic film has a first layer, a second layer and a core layer. The film has activation zones and non-activated zones. The activated zones have sufficient elasticity to stretch to at least 200% while maintaining a permanent set percent of no more than 5%. The non-activated zones have sufficient non-elastic to stretch at least 200% while maintaining a permanent set percent of up to 5%. The activated zones have a tear strength as measured by the Elmendorf Tear Test of 30 g while the non-activated zones have a tear strength as measured by the Elmendorf Tear Test of at least 50 g. The elastic film is particularly useful as an elastic waistband for use in products including absorbent products such as waist bands, side panels and the like. The superior tear-strength of the film prevents tearing during use of the film and promotes longer-lasting applications of the film., In addition, the superior tear-strength of the film prevents existing tears from propagating throughout the film. For ease of illustration, a thin multi-layer coextruded elastomeric film is described in detail herein in FIGS. 1–7. However, this detailed description will allow those skilled in the art to adapt this invention to produce elastomeric film for other applications.

BRIEF DESCRIPTION OF THE DRAWINGS

FIG. 1 is an enlarged cross-section of the film in the present invention.

FIG. 2 is a top plan view of a textured surface of the film of FIG. 1 showing activated zones and non-activated zones.

DETAILED DESCRIPTION OF THE INVENTION

Figure 6:
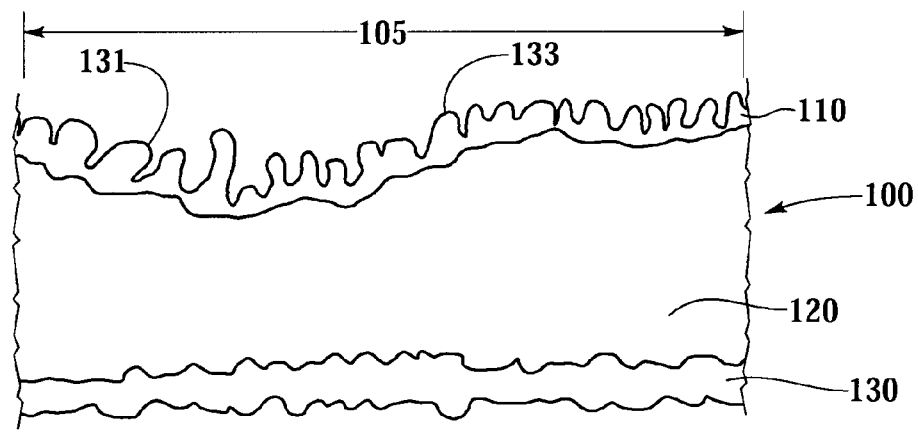
FIG. 6 is an enlarged cross-section of the film of FIG. 1 showing the undulations of the activated zones of the film.
Figure 7:
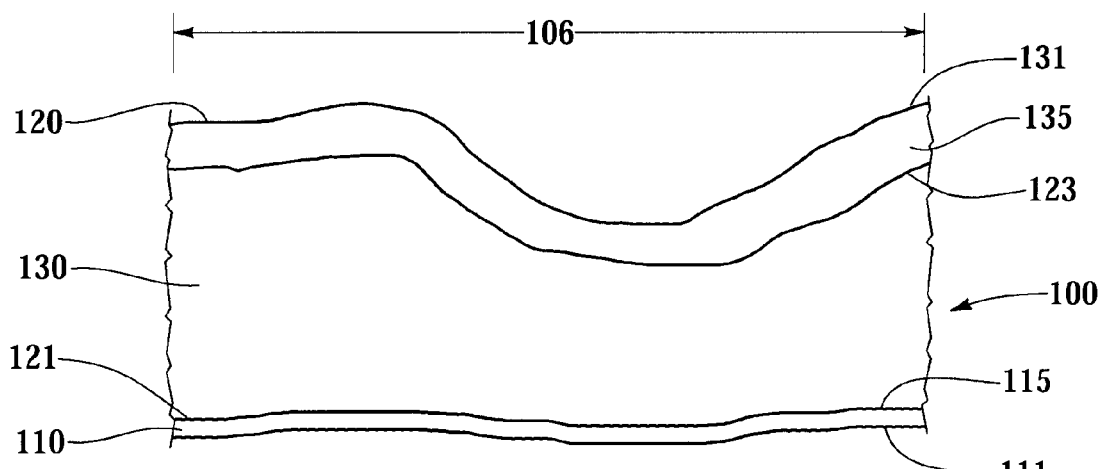
FIG. 7 is an enlarged cross-section of the film of FIG. 1 showing the peaks and valleys of the non-activated zones of the film.

Referring now to the figures, and in particular FIG. 1, FIG. 6, and FIG. 7, there is shown an enlarged cross-section of a film 100. The film 100 is a textured film with a smooth surface 101 and a textured surface 102. The textured surface 102 has texture peaks 103 and texture valleys 104. The film 100 includes activated zones 105 and non-activated zones 106. In one embodiment, the textured surface 102 is an embossed surface. The film 100 includes a first layer 110, a core layer 120 and a second layer 130. The core layer 120 has first core layer surface 121 and a second core layer surface 123. The first layer 110 includes a first layer inner surface 115 adjacent to the first core layer surface 121, and a first layer outer surface 111 which forms the smooth surface 101 of the film 100. The second skin layer 130 includes a second layer inner surface 135 adjacent to the second core layer surface 123 and a second layer outer surface 131 which forms the textured surface 102 of the film 100. The activated zones 105 of the film 100 have undulations 113 and 133 in the first skin layer 110 and the second skin layer 130, respectively.

The core layer 120 is a highly-elastic compound, such as a compound involving at least one or more block copolymers with a hydrogenated diene from the type A-B-A or A-B-A'. Usually such a compound exhibits relatively good elastic recovery or low set from stretching over 100 percent when extruded alone as a single layer. Styrene/isoprene, butadiene or ethylene-butylene/styrene (SIS, SBS, or SEBS) block copolymers are particularly useful. Other useful elastomeric compositions for use as a core layer 120 can include elastomeric polyurethanes, ethylene copolymers such as ethylene vinyl acetates, ethylene/propylene copolymer elastomers or ethylene/propylene/diene terpolymer elastomers. Blends of these polymers alone or with other modifying elastic or non-elastomeric materials are also contemplated as being useful with the present invention. In certain preferred embodiments, the elastomeric materials can comprise such high performance elastomeric material such as Kraton® elastomeric resins from the Shell Chemical Co., which are elastomeric block copolymers. In one embodiment, the film comprises a skin/core/skin weight percentage of 10/80/10 polypropylene skin layer, Kraton® elastomeric resin core layer, and polypropylene skin layer. For applications requiring a thicker film, a skin/core/skin of 15/70/15 percentage by weight may be used. A thicker film may be used advantageously for the following reasons: the film. is less expensive due to the lower percentage of the expensive elastomeric core; a thicker skin allows drawing the film thinner without encountering draw resonance during extrusion; and a thicker skin increases the tear strength of the film as supported in the Tables below.

TABLE 1

ELASTIC FILM PROPERTIES

| Description: | | FILM 1 | FILM 1A | FILM 2 | FILM 2A | FILM 3 | FILM 3A | FILM 4 |
|---|---|---|---|---|---|---|---|---|
| Basis Weight | g/m² | 77.1 | 68.4 | 60 | 53.0 | 70.7 | 45.4 | 68.6 |
| Emb. Caliper, (2") | mils | 4.17 | 3.59 | 3.18 | 2.83 | 4.06 | 10.18 | 3.7 |
| MD Tens. @ 10% | grams | 385 | 529 | 268 | 301 | 688 | 584 | 494 |
| MD Tens @ 25% | grams | 561 | 610 | 421 | 374 | 975 | 640 | |
| MD Tens @ Break | grams | 5681 | 5448 | 3899 | 2139 | 5899 | 3590 | 4621 |
| MD Elongation | % | 725 | 696 | 705 | 546 | 718 | 716 | 773 |
| TD Tens. @ 10% | grams | 323 | 101 | 207 | 52 | 494 | 113 | 54 |
| TD Tens. @ 25% | grams | 448 | 162 | 298 | 91 | 673 | 194 | 3653 |
| TD Tens. @ Break | grams | 5346 | 3920 | 3160 | 2785 | 4952 | 3695 | 753 |
| TD Elongation | % | 829 | 631 | 767 | 696 | 741 | 390 | |
| C.O.F. (Mat'l/Mat'l) | Index | .49/.58 | .79/.57 | 1.30/2.67 | .75/.95 | 1.04/1.78 | .88/.94 | .86/.75 |
| Opacity | % | 91.1 | 86.3 | 84.3 | 79.2 | 73.5 | 64.2 | 74.2 |
| 100% TD Cyclic | | None | 350% | None | None | 350% | None | None | 350% | None |
| 1st Load @ 25% Elong. | grams | 442 | 123 | 170 | 294 | 73 | 89 | 654 | 282 | 193 | 161 |
| 1st Load @ 50% Elong. | grams | 489 | 165 | 217 | 342 | 104 | 117 | 726 | 394 | 255 | 195 |
| 1st Load @ 75% Elong. | grams | 512 | 201 | 243 | 362 | 128 | 134 | 762 | 741 | 323 | 220 |
| 1st Load @ 100% Elong. | grams | 524 | 238 | 267 | 371 | 158 | 150 | 783 | 1202 | 421 | 250 |
| 1st Unload @ 25% | grams | 3 | 24 | 67 | 1 | 24 | 46 | 1 | 23 | 44 | 62 |
| 1st Unload @ 50% | grams | 111 | 65 | 117 | 70 | 52 | 75 | 128 | 118 | 93 | 101 |
| 1st Unload @ 75% | grams | 226 | 105 | 154 | 156 | 75 | 96 | 305 | 236 | 153 | 135 |
| 1st Unload @ 100% | grams | 420 | 196 | 224 | 299 | 133 | 131 | 620 | 907 | 335 | 209 |
| Column Number | | 1 | 2 | 3 | 4 | 5 | 6 | 7 | 8 | 9 | 10 |
| 2nd Load @ 25% Elong. | grams | 188 | 93 | 129 | 100 | 60 | 74 | 232 | 186 | 135 | |
| 2nd Load @ 50% Elong. | grams | 333 | 140 | 183 | 223 | 91 | 103 | 483 | 306 | 196 | |
| 2nd Load @ 75% Elong. | grams | 433 | 181 | 216 | 305 | 117 | 122 | 645 | 576 | 266 | |
| 2nd Load @ 100% | grams | 512 | 231 | 252 | 368 | 154 | 143 | 775 | 1190 | 395 | |
| 2nd Unload @ 25% | grams | -1 | 22 | 65 | 0 | 23 | 45 | 2 | 21 | 43 | |
| 2nd Unload @ 50% | grams | 105 | 65 | 116 | 67 | 51 | 73 | 122 | 120 | 93 | |
| 2nd Unload @ 75% | grams | 226 | 106 | 153 | 158 | 75 | 94 | 312 | 240 | 153 | |
| 2nd Unload @ 100% | grams | 425 | 196 | 220 | 306 | 134 | 129 | 636 | 927 | 333 | |
| 1st Cycle Relaxation | % | 19.9 | 17.7 | 16.0 | 19.4 | 16.2 | 12.7 | 20.8 | 24.5 | 20.3 | 16.2 |
| 2nd Cycle Relaxation | % | 17.2 | 15.1 | 12.7 | 16.9 | 13.0 | 9.5 | 18.0 | 22.1 | 15.7 | 13.5 |
| Hysteresis | % | 2.2 | 3.1 | 5.4 | 1.0 | 2.7 | 5.0 | 1.1 | 1.0 | 6.2 | 5.0 |
| Permanent Set | % | 13.8 | 4.3 | 2.7 | 15.0 | 2.7 | 2.6 | 16.6 | 8.4 | 3.0 | 1.7 |
| Column Number | | 1 | 2 | 3 | 4 | 5 | 6 | 7 | 8 | 9 | 10 |

TABLE 2

Elastic Film Properties: Toughness Measures

| | P.1 | P.2 | 1. | 1. PS | 1. Act. | 2. | 2. PS | 2. Act. | 3. | 3. PS | 3. Act. | 4. | 4. PS | 4. Act. |
|---|---|---|---|---|---|---|---|---|---|---|---|---|---|---|
| Activation Growth⇒ | N/A | N/A | N/A | 39% | 10–15% | N/A | 58% | 10–15% | N/A | 72% | 10–15% | N/A | 72% | 10–15% |
| | Prior Art | | First Sample Set | | | | | | Second Sample Set | | | | | |
| TD @ 25%, g | 154 | 154 | 435 | 107 | 158 | 340 | 94 | 137 | 561 | 293 | 250 | 415 | 206 | 153 |
| TD @ 25%, g | 151 | 154 | 437 | 122 | 247 | 324 | 83 | 105 | 528 | 264 | 247 | 394 | 183 | 143 |
| TD Ultim., g | 1680 | 2452 | 4180 | 5073 | 2991 | 3035 | 3148 | 3054 | 5366 | 5285 | 5001 | 3544 | 4032 | 3496 |
| TD Ultim., g | 1294 | 1419 | 1900 | 1185 | 1783 | 1123 | 653 | 951 | 1905 | 988 | 1757 | 1509 | 801 | 1248 |
| TD Elg., % | 756 | 813 | 747 | 527 | 628 | 751 | 404 | 646 | 800 | 400 | 659 | 776 | 410 | 659 |
| TD Elg., % | 667 | 618 | 587 | 322 | 425 | 527 | 200 | 455 | 524 | 161 | 431 | 542 | 169 | 416 |
| TD Ult/TD25 | 10.9 | 15.9 | 9.6 | 47.4 | 18.9 | 8.9 | 33.5 | 22.3 | 9.6 | 18.0 | 20.0 | 8.5 | 19.6 | 22.8 |
| TD Ult/TD25 | 8.6 | 9.2 | 4.3 | 9.7 | 7.2 | 3.5 | 7.9 | 9.1 | 3.6 | 3.7 | 7.1 | 3.8 | 4.4 | 8.7 |
| Bas. Wt., gsm | 50.7 | 50.2 | 73.5 | N/A | 61.4 | 63.0 | N/A | 46.2 | 76.0 | N/A | 68.2 | 61.1 | N/A | 56.7 |
| MD Tear, g | 15 | 18 | 156 | N/A | 68 | 90 | N/A | 54 | 256 | N/A | 284 | 138 | N/A | 128 |

The First Sample Set material was made of 10/80/10 coextrusion layering and activated 350% in the prestretch and disk assembly activation, the Second Sample Set material was 15/70/15 and activated 250% in prestretch and disk activation.

The first layer 110 and the second layer 130 are polyolefins, and can comprise a blend of polyethylene with Metallocene-catalyzed polyethylene (m-polyethylene) or Metallocene-catalyzed polypropylene (m-polypropylene). If the blends are extruded as a single layer, the blends exhibit poor elastic recovery or high set from stretching over 100 percent. FIG. 2 is a top plan view of the textured surface 102 of the film 100 showing the activated zones 105 and non-activated zones 106. In addition, the textured pattern may be visible over the entire textured surface 102 of the film 100.

As can be seen from FIG. 2, the undulations 113 in the activated zones 105 of the second layer 130 form uniform uni-directional parallel marks in the machine direction in the textured surface 102 of the film 100.

The film 100 has a high coefficient of fiction (COF). It is desirous to have such a high COF to enable successful gripping of the film 100 for stretching and placement in subsequent converting. This is due in part to the non-activated zones 106 remaining non-activated despite stretching the film 100 up to 200%. This property enables the film 100 to exhibit low percent set comparable to the highly elastic core layer 120 while maintaining a coefficient of friction comparable to a polyolefin elastomeric film. Other films often require a slip additive, which results in a lower COF. The slip additive prevents the films from sticking during film collection and dispension. Unfortunately, the slip additive and resulting lower COF hinders the mechanical or vacuum-assisted stretching process.

Figure 3:
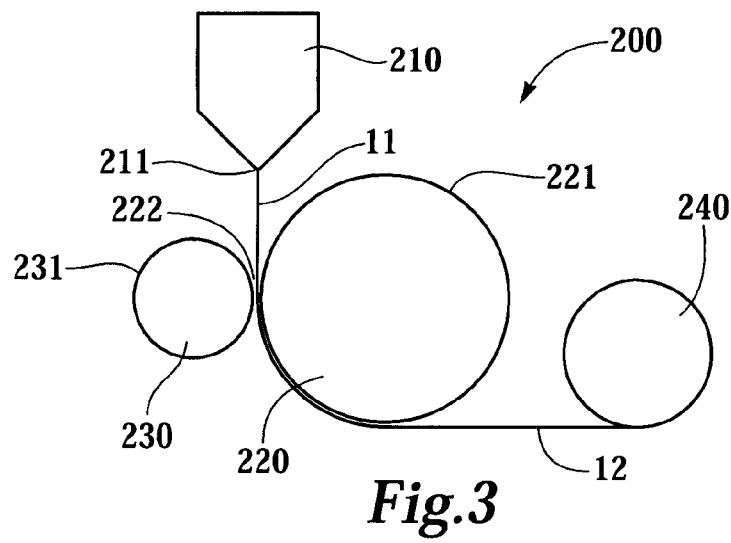
FIG. 3 is a simplified schematic illustration showing the embossed stretch film forming process of the present invention.

FIG. 3 is a simplified block diagram illustrating a forming process 200 for forming the embossed stretch film 100 of the invention. A cast coextrusion 11 of the skin/core/skin exits coextruder 210 through coextrusion slot die 211. Prior to hardening, cast coextrusion 11 is delivered at an elevated temperature as a molten or semi-molten plastic to an engraved roll 220. In certain embodiments, the cast coextrusion 11 exits the coextruder 210 at a temperature of about 350° F. to about 650° F. (175° C. to 315° C.). The melt temperature of the polymer resin is about 400° F. to about 475° F. The embossed coextrusion 12 is then collected onto embossed film roll 240. Engraved roll 220 has a smooth surface 221 which engages cast coextrusion 11 and moves cast coextrusion 11 into contact point 222 of backup roll 230. Backup roll 230 has embossing surface 231 for delivering an embossed pattern to emboss the cast coextrusion 11 forming an embossed coextrusion 12.

In the embodiment shown, the cast coextrusion 11 is preferably extruded through the slot die 211 at a distance of about 1 to about 10 inches, and most preferably about 2 to about 6 inches, from engraved roll 220. The pressure between the backup roll 230 and engraved roll 220 causes the embossed coextrusion 12 to retain the embossed pattern from the embossing surface 231. The engraved roll 220 or the backup roll 230 can be temperature controlled to add heat or cooling of the polymer resin as desired. However, it is to be understood that other temperature control means can be used to adjust the temperature of the polymer resin at this point.

As illustrated in FIG. 3, the film 100 is formed without the use of adhesives. The lowest melting layer of the cast coextrusion 11 is molten or semi-molten, which means that the thermoplastic melt stream of the elastomeric film material is at a temperature above the temperature of melting ($T_m$) of the thermoplastic film material. The temperature of melting of polymers is determined on a differential scanning calorimeter. When the polymer stream is in the molten or semi-molten phase, the polymer is amorphous; that is, molecules comprising the elastomeric polymer are free to move about, particularly when influenced by outside forces such as a pressure differential. Portions of the embossed coextrusion 12 that form the textured surface 102 of the film 100 retain the embossed pattern due to the pressure differential between the backup roll 230 until the cast coextrusion 11 at least partially sets or crystallizes. At that time, the embossed coextrusion 12 is no longer formable and retains its new shape. This phase is known as the temperature crystallinity (Tc) and is also determined by a differential scanning calorimeter. After the cast coextrusion 11 is embossed, the cast coextrusion 11 releases enough heat energy to move below the temperature of crystallinity while still being held in its new (embossed coextrusion 12) shape by the pressure differential.

As described herein, the final film 100 is embossed. However, instead of a backup roll 230, an air knife (not shown), wherein air is blown onto the cast coextrusion 11 prior to the contact point 222, may be used to quench the cast coextrusion 11 without an embossed pattern. This may draw the cast coextrusion 11 thinner and thereby reduce manufacturing costs. Alternatively, a vacuum box (not shown) may be placed inside engraved roll 220 to draw the cast coextrusion 11 over the surface of the engraved roll 220 and quench the molten web. The embossed pattern as described herein penetrates into the cast coextrusion at a depth of about 1.5 to 2.5 mils. The backup roll 230 has a temperature control for controlling how quickly the film 100 cools. In the forming process 200, the temperature of the backup roll 230 is preferably in the range of 90° F. to 140° F. If the cast coextrusion 11 is allowed to cool too slowly, the cast coextrusion 11 may become brittle. In the preferred embodiment, the embossed coextrusion 12 has an embossed maximum width of about 6 mils.

It is to be understood that there are elastomeric polymers with different melt temperatures and that the distance between the coextrusion slot die 211 and the contact point 222 can be varied based on the parameters defined by the use of a particular polymer. Thus, the contact point 222 of the film 100 will depend on the melting temperature of the specific polymer in use at the time.

Figure 4:
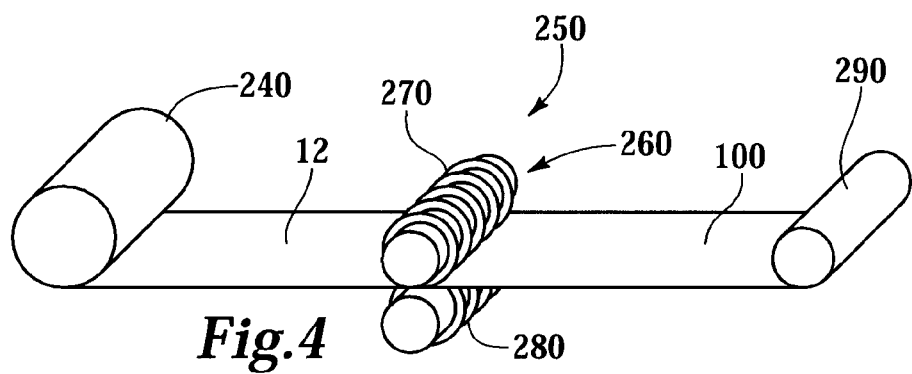
FIG. 4 is a simplified schematic illustration showing the activation process of the present invention.

Referring now to FIG. 4, an activation process 250 is shown. The embossed coextrusion 12 is fed from the embossed film roll 240 through parallel disk assemblies 260. The embossed coextrusion 12 is then collected onto the activated film roll 290.

Figure 5:
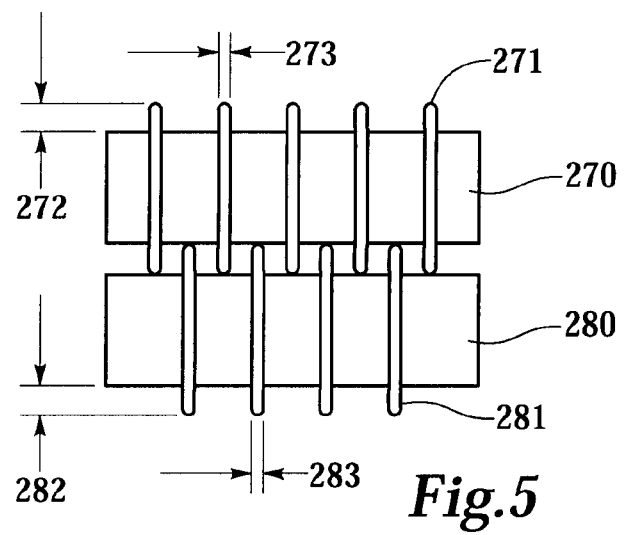
FIG. 5 is an enlarged side view of the lower disk assemblies used to activate the film of FIG. 1 during the activation process of FIG. 5.

In the embodiment shown, an upper disk assembly 270 includes circumferentially spaced ridges 271. Ridges 271 have an engagement height 272 and an engagement width 273. Ridges 271 are equally spaced along the circumference of upper disk assembly 270. Lower disk assembly 280 opposes upper disk assembly 270. Lower disk assembly 280 includes ridges 281 having an engagement height 282 and an engagement width 283. Ridges 271 of upper disk assembly 270 and ridges 281 of lower disk assembly 280 are alternately spaced along the respective circumferences of assemblies 270, 280 such that the embossed coextrusion 12 passes through each ridge independently. Ridges 281 are equally spaced along the circumference of lower disk assembly 280. Assemblies 270, 280 are shown in greater detail in FIG. 5. In the present embodiment, as the embossed coextrusion 12 travels through ridges 271, 281, the embossed coextrusion 12 is stretched and elongated and becomes corrugated onto the core layer 120 (FIG. 6). In certain preferred embodiments, the depth of engagement of the ridges 271, 281 is in the range of 165 to 230 mils, which is much deeper than conventional ridges known to be used in the art. Ridges 271, 281 in a preferred embodiment are 27 mils. wide and are spaced apart by 49.5 mils. While traveling through the ridges 271, 281, the embossed coextrusion 12 is subjected to stretching in a way such that only small, discreet and narrow longitudinal strip regions of the embossed coextrusion 12, not exceeding 1 inch in width, are elastically overstrained in order to significantly decrease the thickness of the skin layer in these regions compared to the thickness of the skin layers in the adjacent regions. This can be seen in more detail in FIGS. 1 and 2. The elastic overstraining occurs by applying a relatively high strain rate to extension ratio of at least 350 percent while adjacent regions located between the strips are strained from 10 percent to 200 percent. The combination of the high strain rate and the high extension causes extreme thinning of the polyolefinic elastomeric layers in the narrow strip region that were overextended. This effect, in turn, enables the activated zones 105 to behave more like core layer 120, which will become the predominant elastomer. The resulting multi-layer film 100 exhibits elastic properties comparable to the core layer 120, i.e., a very low percent set. Surprisingly, the film 100 exhibits an overall tear-strength value as measured by the Elmendorf Tear test well above conventional films in the art. The tear-strength of the film 100 is important during conversion of the finished film 100 to final products. Namely, when an initial cut is made on the film 100 for incorporation into a product, the cut is sometimes non-uniform and leaves jagged edges. A film having a sufficiently high tear-strength will prevent propagation of any tears that result from the initial cutting of the film. The film 100 of the present invention has a tear-strength that is much superior to conventional films used in the art. In addition to other advantages described herein, the film 100 will last much longer in applications due to the tear-resistance inherent in the film 100. The film 100 continues to exhibit a coefficient of a friction (COF) comparable to a polyolefin elastomer film. The COF value enables the film 100 to be easily manipulated during post-formation manufacturing processes.

The activation process 250 may be combined with film forming process 100 to eliminate the steps of collecting the embossed coextrusion 12 and re-feeding the embossed coextrusion 12 through parallel disk assemblies 260. In this embodiment, the embossed coextrusion 12 would proceed to the parallel disk assemblies 260 after the embossed pattern has been formed in the embossed coextrusion 12.

The film 100 has several advantages. First, skin layers may be coextruded using the process of the invention that are much thinner than conventional skin layers. The thinness of the material enhances the overall elasticity of the film 100.

Second, the tear-strength of the skin layers of the present invention is critical to the overall properties of the film 100. The superior tear-strength of film 100 is required for mechanical activation of the film 100 at the very high ridge penetration depth as the film 100 passes through disk assemblies 260 during the activation process 250. The use of a less tear-resistant film would significantly hinder mechanical activation by limiting the depth ridges 271, 281 are allowed to penetrate into the film 100. Because the film 100 is exceedingly tear-resistant, the skin layers 110, 130 are thinner and activate readily. The film 100 may subsequently stretch with strong retractive forces and recover with very low setting.

Third, the film 100 is surprisingly resistant to tear propagation, which is useful in certain applications. In some applications, a user ultrasonically or by other means pits the film 100 in order to increase film breathability. During use of the application, the film 100 may be under constant or varying degrees of tension. A less tear-resistant film would not protect the areas around any pits formed prior to film usage and thus the film would be subject to increased tear propagation. The tear resistance of the present invention would sufficiently resist such propagation and extend the usefulness of the film.

Fourth, the skin layers 110, 130 have high compatibility with the core layer 120. This allows skin layers 110, 130 to remain in intimate contact with the core layer 120 during activation, whereby skin layers 110, 130 do not separate or rupture from the core layer 120. The thinner activated zones 105 thus retain and behave more like the highly-elastic core layer 120.

Finally, the skin layers in the present invention have a sufficiently high COF comparable to polyolefin elastomeric films to allow handling of the film 100 via mechanical gripping or vacuum-assisted gripping.

Table 1 shows the films prior to activation through the disk assemblies 260 and post-activation by the application of the film through the disk assemblies 260. As can be seen, the permanent set percent significantly decreases after activation. In the data set forth in Table 1 above, elastic hysteresis is used to quantify elastic performance. The high performance elastic behavior is defined by tensile set less than about 10 percent and force relaxation less than about 20 percent after 300 percent elongation. The procedure to measure hysteresis of a sample is as follows:

1. A sample of the film or laminate is placed. in the jaws of a tensile testing machine.
2. The sample is pulled a first time (cycle 1 elongation) at the rate of 20 inches per minute to the desired elongation (for example, 200 percent)
3. The force upon reaching the desired elongation is noted.
4. The sample is held at the desired elongation for 30 seconds after which the force is noted.
5. The instrument is returned to its initial position (zero elongation)
6. The sample is held in a relaxed state for 30 seconds.
7. The sample is pulled a second time (cycle 2 elongation) at the rate of 20 inches per minute to the desired elongation. The amount of movement in. the tensile testing machine jaw before the film exerts any force is noted.
8. The sample is held at the desired elongation for 30 seconds and then relaxed.

Tensile set is a measure of the permanent deformation of the sample as a result of the initial elongation, hold, and relax cycle. Specifically, tensile set is the elongation measured in the second cycle divided by the initial sample length (2 inches).

The transverse direction (TD) force at 10 percent elongation is a measure of the force required to extend the film 10 percent in the transverse (i.e., cross machine) direction. The tensile properties (TD force) were measured using the ASTMD-882 method. In the present application, the machine direction (MD) is defined as the direction in which the film is moved through the processing. The transverse (or cross machine) direction is the direction perpendicular or transverse to the machine direction.

Films 1 and 1A, 2 and 2A, and 3 and 3A are of identical composition. Films 1 and 1A have a modified SEBS core having a draw resonance limit of about 75 grams per square meter. Films 2 and 2A are identical except that they employ a softer grade core and have a draw resonance limit of about 60 grams per square meter. Films 3 and 3A are produced with a very low cost formulation comprising SIS and polyethylene. Film 4 has a core composed of SIS/PE having a draw resonance limit of about 69 grams per square meter. For film 1 and film 2, readings are given for no activation, and for activation using an Instron tensile tester wherein the film is elongated to 350 percent extension. As can be seen from the Table, the permanent set for the ring rolled film 1A, 2.7 percent, is significantly less than film 1, wherein the film was activated using the Instron tensile tester, resulting in a 4.3 permanent set. Likewise, the permanent set for film 2A, 2.6 percent, is less than the permanent set for film 2 activated with the tensile tester at 2.7 percent. Film 3A also showed a dramatic decrease in percent permanent set of 3.0 percent versus the percent set of the same film using an Instron tensile tester at 8.4 percent. And the lowest cost film, depicted as Film 4, showed remarkably low permanent set percent of 1.7.

The tear-strength of the film material, depicted in Table 2, shows properties of skin layers 110, 130 in comparison to conventional skin layers. An Elmendorf Tear Test was used to measure the toughness of the film. As used herein, the Elmendorf Tear Test refers to the procedure to measure the toughness of the film, and is in accordance with ASTMD 1922 method, entitled *Standard Test Method for Propagation Tear Resistance of Plastic Film and Thin Sheeting by Pendulum Method.*

As illustrated, Table 2 depicts three sets of data: prior art samples; a first sample set of the present invention using a 10/80/10 skin/core/skin weight percentage; and a second sample set of the present invention using a 15/70/15 weight percentage. The columns are labeled in the following manner: P. 1 and P. 2 refer to prior art sample 1 and 2, respectively; 1., 1. PS, 1. Act. refer to first sample set 1 prior to stretching, first sample 1 after pre-stretching, and first sample 1 activated using the disk assemblies. The references for 2, 3 and 4 have identical column references save for the sample number.

Activation growth refers to the amount the respective sample grew after activating the film. TD (transverse direction) @ 25%, is a measure of the force required to extend the film 25 percent in the transverse (i.e., cross machine) direction. Likewise, TD Ultim. is a measure of the ultimate force (tensile strength) of the respective sample at the breaking point. TD Elongation % is the percentage the film has stretched at TD Ultimate. TD Ult/TD25 is a ratio of the forces from TD Ultim. and TD @ 25%. The basis weight, in grams/square meter is given for each film. The tear strength (MD Tear) as measured by the ASTMD 1922 method is shown at the bottom of Table 2.

The first sample set was activated 350% in the prestretch and disk assembly activation whereas the second sample set was activated 250% in the prestretch and disk assembly activation.

As can be seen in Table 2, the tear strength for the fully activated films of the present invention (Columns 1. Act, 2. Act., 3 Act. and 4 Act.) show significantly higher tear strength than prior art films. For example, Samples 1 and 2 Act. each have a tear strength of 68 grams and 54 grams, respectively. In comparison, prior art films show tear strengths of 15 and 18 grams. The present invention films therefore provide significantly higher tear resistance by factors of 4 or greater.

This property is especially advantageous for use in elastic waistbands and in products including absorbent products and the like, which are often subjected to tearing during manufacturing and consumer use. The increased tear resistance will prevent further tearing and therefore increase the life of the product.

While the present invention has been described primarily in the context of absorbent products and the like, it is recognized that the present invention may also be applied to many other applications and environments. For example, the present invention is particularly well-suited for use with disposable articles using the film of the present invention as a waistband component or side panel component. It will be obvious to those skilled in the art that various changes and modifications can be made without departing from the spirit and scope of the present invention, and it is intended to cover the claims appended hereto. All such modifications are within the scope of this invention.

What is claimed is:

1. A tear-resistant low set elastic film, comprising:
   a first layer;
   a second layer;
   a core layer bonded between said first layer and said second layer;
   activated zones in said film that have sufficient elasticity to stretch at least 200% while maintaining a permanent set percent of no more than about 5%;
   non-activated zones in said film that have sufficient non-elasticity to stretch at least 200% while maintaining a permanent set percent of up to about 5%;
   wherein said activated zones in said film have a tear-strength as measured by an Elmendorf Tear Test of at least 30 g; and
   wherein said non-activated zones in said film have a tear-strength as measured by an Elmendorf Tear Test of at least 50 g.

2. The tear-resistant low set elastic film of claim 1, wherein said activated zones of said film have a tear-strength as measured by the Elmendorf Tear Test in the range of 30 g to 400 g.

3. The tear-resistant low set elastic film of claim 1, wherein said non-activated zones of said film have tear-strength as measured by the Elmendorf Tear Test in the range of 30 g to 400 g.

4. The tear-resistant low set elastic film of claim 1, wherein said film may be stretched to at least 200% of an initial width in a transverse direction of said film without detachment of said first layer and said second layer from said core layer.

5. The tear-resistant low set elastic film of claim 1, wherein said activated zones of said film have a width of about 2/64 inch in a transverse direction.

6. The tear-resistant low set elastic film of claim 1, wherein said activated zones of said film have a width in a range between 2/64 inch and 4/64 inch and a transverse direction.

7. The tear-resistant low set elastic film of claim 1, wherein said non-activated zones of said film have a width of about 1/128 inch in a transverse direction.

8. The tear-resistant low set elastic film of claim 1, wherein said non-activated zones of said film have a width in the range between 1/128 inch and 1/64 inch in a transverse direction.

9. The tear-resistant low set elastic film of claim 1, wherein said first layer and said second layer are comprised of polyolefins.

10. The tear-resistant low set elastic film of claim 1, wherein said core layer is a highly elastic compound involving at least one block co-polymer.

11. The tear-resistant low set elastic film of claim 1, wherein said first layer and said second layer are comprised of a blend of polyethylene.

12. The tear-resistant low set elastic film of claim 1, wherein said first layer and said second layer are comprised of a blend of Metallocene-polyethylene.

13. The tear-resistant low set elastic film of claim 1, wherein said core layer is a hydrogenated diene selected from a group consisting of type A-B-A and type A-B-A'.

14. The tear-resistant low set elastic film of claim 1, wherein said core layer is a co-polymer selected from a group consisting of a styrene/isoprene block co-polymer, a butadiene block co-polymer, and an ethylbutylene/styrene block co-polymer.

15. The tear-resistant low set elastic film of claim 1, wherein said core layer is a copolymer selected from a group consisting of an elastomeric polyurethane copolymer and an ethylene copolymer.

16. The tear-resistant low set elastic film of claim 1, wherein said core comprises a blend of block co-polymers.

17. The tear-resistant low set elastic film of claim 1, wherein said core comprises a blend of a block co-polymer and a modifying elastic material.

18. The tear-resistant low set elastic film of claim 1, wherein said core comprises a blend of a block co-polymer and a modifying non-elastic material.

19. The tear-resistant low set elastic film of claim 1, wherein said film is embossed.

20. The tear-resistant low set elastic film of claim 1, wherein said film has a permanent set percent in the range of 0 to about 5%.

21. A tear-resistant low set elastic film, comprising:

a first layer of Metallocene-polyethylene;

a second layer of Metallocene-polyethylene;

a core having a blend of block-coplymers co-extruded between said first layer and said second layer;

activated zones in said film;

non-activated zones in said film, said non-activated zones having a greater tear-resistance than said activated zones;

wherein said film has sufficient elasticity to stretch at least 200% of an initial width in a transverse direction while maintaining a permanent set percent of no more than about 5%;

wherein said non-activated zones maintain a permanent set percent of no more than about 5% when said film is stretched up to 200% of an initial width in a transverse direction, said activated zones having a width in a range of about 2/64 inch to about 4/64 inch, wherein said non-activated zones have a width in the range of about 1/128 inch to about 4/64 inch;

wherein said activated zones in said film have a tear-strength as measured by the Elmendorf Tear Test of at least 30 g;

wherein said non-activated zones of said film have a tear-strength as measured by the Elmendorf Tear Test of at least 50 g;

wherein said film is embossed; and wherein said film has a permanent set in a range of 0 to about 5%.

\* \* \* \* \*

UNITED STATES PATENT AND TRADEMARK OFFICE
CERTIFICATE OF CORRECTION

PATENT NO. : 6,472,084 B1
DATED : October 29, 2002
INVENTOR(S) : Jeffrey A. Middlesworth et al.

It is certified that error appears in the above-identified patent and that said Letters Patent is hereby corrected as shown below:

Column 1,
Line 34, replace "film.," with -- film. --

Column 2,
Line 54, replace "film. is" with -- film is --

Column 8,
Line 9, replace "placed. in" with -- placed in --
Line 23, replace "in. the" with -- in the --

Column 10,
Line 18, after "have" insert -- a --
Line 20, replace "30" with -- 50 --
Line 31, replace "4/64 inch and" with -- 4/64 inch in --

Signed and Sealed this

Twenty-fifth Day of November, 2003

JAMES E. ROGAN
*Director of the United States Patent and Trademark Office*